United States Patent
Foster

(10) Patent No.: US 10,195,324 B2
(45) Date of Patent: Feb. 5, 2019

(54) BEARING FOR A CARDIAC PUMP

(71) Applicant: CALON CARDIO-TECHNOLOGY LTD., Swansea, West Glamorgan (GB)

(72) Inventor: Graham Foster, West Glamorgan (GB)

(73) Assignee: CALON CARDIO-TECHNOLOGY LTD., Swansea (GB)

(*) Notice: Subject to any disclaimer, the term of this patent is extended or adjusted under 35 U.S.C. 154(b) by 0 days.

(21) Appl. No.: 14/895,822

(22) PCT Filed: May 21, 2014

(86) PCT No.: PCT/GB2014/051561
§ 371 (c)(1),
(2) Date: Dec. 3, 2015

(87) PCT Pub. No.: WO2014/195675
PCT Pub. Date: Dec. 11, 2014

(65) Prior Publication Data
US 2016/0121034 A1 May 5, 2016

(30) Foreign Application Priority Data
Jun. 7, 2013 (GB) .................................. 1310199.3

(51) Int. Cl.
*A61M 1/10* (2006.01)
*A61M 1/12* (2006.01)

(52) U.S. Cl.
CPC ........ *A61M 1/1017* (2014.02); *A61M 1/1013* (2014.02); *A61M 1/101* (2013.01); *A61M 1/1022* (2014.02); *A61M 1/122* (2014.02)

(58) Field of Classification Search
CPC .... A61M 1/101; A61M 1/122; A61M 1/1031; A61M 1/1034; A61M 1/127;
(Continued)

(56) References Cited

U.S. PATENT DOCUMENTS 5,399,074 A 3/1995 Nose et al.
5,947,703 A 9/1999 Nojiri et al.
(Continued)

FOREIGN PATENT DOCUMENTS

EP 1027898 A1 8/2000
GB 2347085 A 8/2000
(Continued)

OTHER PUBLICATIONS

Internationational Preliminary Report on Patentability for PCT/GB2014/051561, dated Dec. 17, 2015 (8 pages).
(Continued)

*Primary Examiner* — Deborah Malamud
(74) *Attorney, Agent, or Firm* — Harness Dickey

(57) ABSTRACT

A plain bearing assembly for a cardiac pump, the plain bearing assembly comprising; a rotational portion which, in use, rotates with a cardiac pump rotor, the rotational portion configured to engage a stationary portion of a cardiac pump housing, the stationary portion comprising one or more first bearing surfaces and the rotational portion comprising one or more second bearing surfaces, the one or more second bearing surfaces configured so as to be in contact with the one or more first bearing surfaces, therein defining a bearing interface between the one or more first bearing surfaces and the one or more second bearing surfaces during rotation of the rotational portion, wherein the rotational portion comprises one or more first flow channels configured to interrupt the bearing interface and permit blood to flow between an outside of the plain bearing assembly and a center of the plain bearing assembly.

21 Claims, 11 Drawing Sheets

(58) Field of Classification Search
CPC .............. A61M 1/1029; A61M 1/1086; A61M 2210/125; A61M 1/1012; A61M 2205/103; A61M 1/1013; A61M 1/10; A61M 1/1049; A61B 5/02141; A61B 5/4836; F04D 13/0633; F04D 13/06; A61F 2/24; Y10S 415/90; Y10T 29/49012; Y10T 29/49236
See application file for complete search history.

(56) References Cited

U.S. PATENT DOCUMENTS

| | | | |
|---|---|---|---|
| 5,957,672 A | 9/1999 | Aber | |
| 7,762,941 B2 | 7/2010 | Jarvik | |
| 7,959,551 B2 | 6/2011 | Jarvik | |
| 8,088,059 B2 | 1/2012 | Jarvik | |
| 2003/0113208 A1 | 6/2003 | Hart et al. | |
| 2008/0269880 A1 | 10/2008 | Jarvik | |
| 2010/0174131 A1 | 7/2010 | Foster et al. | |
| 2011/0124950 A1 | 5/2011 | Foster | |
| 2011/0144413 A1 | 6/2011 | Foster | |
| 2012/0088954 A1 | 4/2012 | Foster | |

FOREIGN PATENT DOCUMENTS

| | | |
|---|---|---|
| GB | 2451161 A | 1/2009 |
| WO | WO-2010/015836 A1 | 2/2010 |
| WO | WO-2013/011308 A1 | 1/2013 |

OTHER PUBLICATIONS

Search Report issued in UK Patent Application No. 1210199.3 dated Nov. 28, 2013.
Internationational Search Report and Written Opinion of the ISA for PCT/GB2014/051561, ISA/EP, Rijwsijk, NL, dated Oct. 9, 2014 (11 pages).

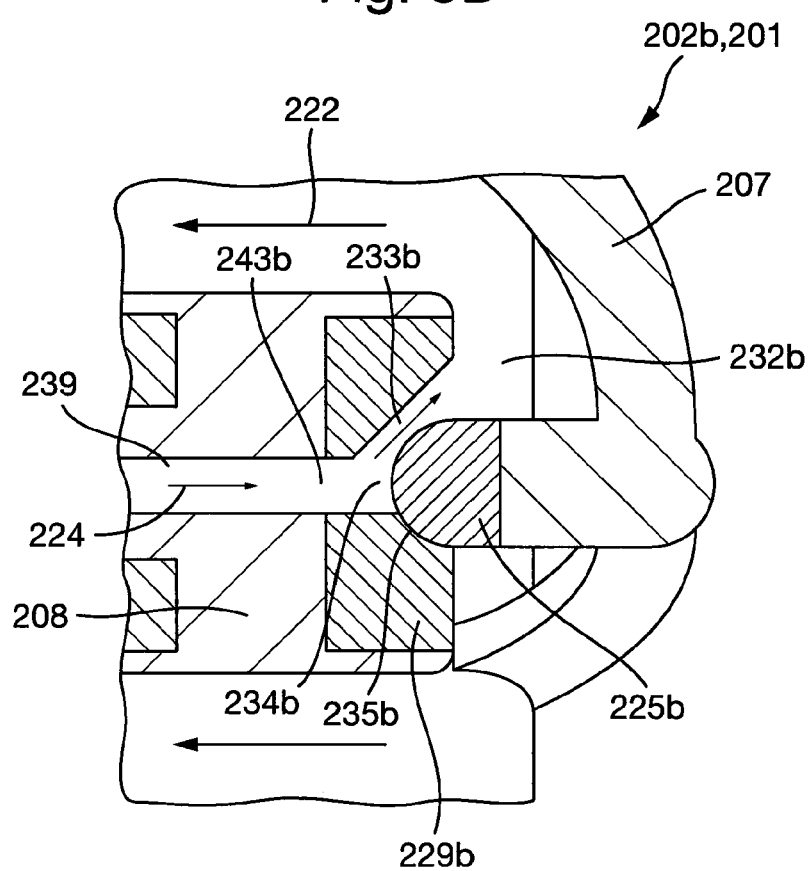

BEARING FOR A CARDIAC PUMP

CROSS-REFERENCE TO RELATED APPLICATIONS

This application is a 371 U.S. National Stage of International Application No. PCT/GB2014/051561, filed May 21, 2014, which claims the benefit of and priority to British Patent Application No. 1310199.3, filed Jun. 7, 2013. The disclosures of the above applications are incorporated herein by reference.

This invention relates to a bearing assembly for a cardiac pump and particularly, but not exclusively relates to a bearing assembly for a cardiac pump that mitigates the risk of the deposition of biological material in areas proximate to the bearing assembly.

BACKGROUND

Heart failure is a major global health problem resulting in many thousands of deaths each year. Until recently, the only curative treatment for advanced heart failure has been a heart transplant or an implantation of a Total Artificial Heart (TAH). Unfortunately, the number of donor heart's only meets a tiny fraction of the demand and TAHs have yet to gain widespread acceptance due to the inherent technical difficulties.

Ventricular Assist Devices (VAD) have been gaining increased acceptance over the last decade, primarily as bridge-to-transplant devices. VADs are designed to be long-term implants and work alongside a diseased heart to boost its output and keep the patient alive and/or give a better quality of life whilst awaiting transplant.

The use of VADs has shown that, in most cases, once the device has been implanted, the heart failure does not progress any further and the patient regains a good quality of life. In cases where a heart transplant has not been available, patients have lived for several years using VAD therapy without major complications. Therefore, a VAD can be considered a viable alternative to heart transplantation and offers hope to the many thousands of heart failure patients for whom a donor heart will not be available.

At present, the main reasons preventing VADs from being fitted on a routine basis are the invasive surgical procedure required to fit the devices, and the high cost of the devices themselves. With regard to the surgery, typically a sternotomy and a full heart-lung bypass are required to fit a VAD, together with major procedures to the heart, thoracic aorta and abdominal cavity. Presently, the risk of such an operation cannot be justified except in the case of those in the most advanced stages of heart failure. With regard to cost, current devices are typically of complex construction and require specialised and expensive manufacturing processes for their construction. The surgery required to lit them is also expensive owing to long and intensive operative procedures.

If the long term implantation of a VAD or an equivalent circulatory assist device could be achieved with a less invasive surgical procedure (e.g. by eliminating any procedures to the abdominal cavity, the need for a sternotomy and/or a heart-lung bypass) and the cost of the devices could be significantly reduced, then the use of VADs to treat heart failure could become far more widespread and routine.

The key to a less invasive implantation procedure for a VAD is to make the device small enough so that it can be comfortably implanted entirely within the pericardial space, eliminating the need for any procedures to the abdominal cavity. Furthermore, a device small enough to be implanted via a thoracotomy, as opposed to a full sternotomy, would be beneficial for those cases where this approach is suitable.

It is also important to minimise surgical risks so it is beneficial to use existing proven to improving on them where possible. A well-proven method of implanting current VADs is attaching the devices directly to the apex of the left ventricle, with an inlet to the device residing within the ventricle and the outlet of the device sitting outside of the heart. This eliminates the need for a separate inflow cannula, reducing the potential for complications. The workings of the pump (impeller, motor, etc.) may reside mostly within the ventricle, across the ventricle wall, or mostly outside of the ventricle depending on the design of the device.

In general terms, a cardiac pump suitable for implantation into a ventricle of a human heart, is known. It is also known for the cardiac pump to comprise a housing comprising an inlet for blood, an outlet for blood and a primary blood flow path, which extends between the inlet and the outlet, and a cardiac pump rotor disposed within the housing for causing blood to flow along the primary flow path from the inlet to the outlet.

In such known devices, the cardiac pump rotor may be rotatably coupled to the housing about plain bearing assemblies. One of the most important factors in the design of a VAD is the passage of blood through the cardiac pump, particularly the passage of blood in the region of the bearings. The regions of blood flow around the bearings, i.e. the regions around circumferential transition between the rotating and stationary components, may be areas of flow stasis and therefore predisposed to thrombus formation or indeed any type of protein deposition. It is particularly important, therefore, that bearings are well washed with a constant supply of fresh blood as the heat generated and geometrical constraints in these areas make them particularly prone to thrombus formation and/or pump deposition.

Therefore, it is desirable to directly expose the interface between rotating and stationary components to a continuous supply of blood flow, such that the proteinaceous and cellular components of the blood responsible for pump deposition and thrombus formation are prevented from aggregating in this region.

U.S. Pat. No. 8,088,059 B2 discloses an axial cardiac pump. A pump similar to that disclosed in U.S. Pat. No. 8,088,059 B2 and known as Jarvik 2000 has supported a patient for seven years and uses blood immersed bearings washed by high flow to avoid excessive thrombus formation. This permits the pump to be very simple and small. Nonetheless, the present Jarvik 2000 bearings and all other mechanical blood immersed bearings of the prior art have a supporting structure that may be susceptible to thrombus adjacent to the bearings.

U.S. Pat. No. 5,399,074 A discloses centrifugal blood pump, used for heart-lung machines or the like, which comprises an impeller, a casing having a suction inlet and a delivery outlet and being equipped with a space for rotatably accommodating the impeller, and a magnetic drive means disposed outside the casing. The impeller is of a rotationally symmetric shape and has a rotary vane section and a cylindrical section equipped with a magnet means. The magnet drive means for generating a rotating magnetic field coaxially encloses the magnet means of the above-mentioned cylindrical section and rotates the impeller in cooperation with the magnet means. At least the end section of the impeller's rotation centre on the rotary vane section side is supported preferably by a pivot bearing. However, the pump disclosed in U.S. Pat. No. 5,399,074 A may also be susceptible to thrombus formation in the regions surrounding the bearings.

The present invention therefore seeks to address these issues.

STATEMENTS OF INVENTION

According to the present invention there is provided a plain bearing assembly for a cardiac pump, plain bearing assembly comprising a first bearing portion. The first bearing portion is configured to engage a second bearing portion. One of the first bearing portion and the second bearing portion is configured to rotate with a cardiac pump rotor. The first bearing portion comprises one or more first bearing surfaces and the second bearing portion comprises one or more second bearing surfaces. The one or more first bearing surfaces are configured so as to be in contact with the one or more second bearing surfaces so as to define a bearing interface between the one or more first bearing surfaces and the one or more second bearing surfaces during rotation of the cardiac pump rotor. The first bearing portion comprises one or more first flow channels configured to interrupt the bearing interface and permit blood to flow between an outside of the plain bearing assembly and a centre of the plain bearing assembly for the purpose of washing the bearing interface and preventing the deposition of proteins and/or the formation of thrombi.

The one or more first flow channels may be formed by one or more gaps between a non-axisymmetric first bearing surface, e.g. a polyhedron, wherein the non-axisymmetric first bearing surface may possess one or more degrees of rotational symmetry, and an axisymmetric second bearing surface, e.g. a ball or a cone. The one or more first bearing surfaces may be configured to at least partially form the shape of a pyramid. The one or more first bearing surfaces may be configured to form a recess in the first bearing portion. The recess may be at least partially of the form of the shape of a pyramid, e.g. a pyramid with a polygonal base, a truncated pyramid and/or a frustum.

The outside of the plain bearing assembly may be a region radially outside the plain bearing assembly. The centre of the plain bearing assembly may be a region radially inside the plain bearing assembly.

The first bearing may further comprise an opening extending axially through the first bearing portion. The opening may be configured to intersect the one or more first flow channels and permit blood to flow through the first bearing portion. The second bearing portion may comprise further opening extending axially through the second bearing portion.

The one or more first bearing surfaces and the one or more second bearing surfaces may be substantially conformal. The one or more first flow channels may be formed by one or more grooves through the one or more first bearing surfaces.

The plain bearing assembly may comprise at least a partial ball and socket bearing. The plain bearing assembly may comprise at least a partial ring and cone bearing. The plain bearing assembly may be further configured such that one or more of the first bearing surfaces forms a continuous surface with one or more walls of the adjacent one or more first flow channels.

A cardiac pump may comprise one or more of the above-mentioned plain bearing assemblies. The cardiac pump may further comprise a primary flow path and one or more secondary flow paths, the secondary flow paths being at least partially configured to fluidically connect two or more regions of the primary flow path. The one or more first flow channels in the plain bearing assembly may at least partially form the secondary flow path. The cardiac pump rotor may comprise one or more second flow channels that extend through the cardiac pump rotor. The one or more second flow channels may extend axially and/or radially through the cardiac pump rotor. The one or more second flow channels may extend through the cardiac pump rotor at any orientation. The one or more second flow channels may be curved or straight. The one or more second flow channels in the cardiac pump rotor may at least partially form the secondary flow path.

The one or more first flow channels in the plain bearing assembly may be fluidically connected to the one or more second flow channels in the cardiac pump rotor. The one or more second flow channels may be configured to extend through the cardiac pump rotor and be fluidically connected with the one or more first flow channels, such that blood may flow between the outside of the plain bearing assembly and the one or more second flow channels through the cardiac pump rotor for the purpose washing the bearing interface and preventing the deposition of proteins and/or the formation of thrombi.

The cardiac pump may further comprise a first plain bearing assembly and a second plain bearing assembly. The one or more second flow channels of the cardiac pump rotor may fluidically connect the one or more first flow channels of the first plain bearing assembly to the one or more first flow channels of the second plain bearing assembly, such that blood may flow between the outside of the first plain bearing assembly and the outside of the second plain bearing assembly for the purpose of washing the bearing interface and preventing the deposition of proteins and/or the formation of thrombi.

According to a further aspect of the present invention there is provided a cardiac pump comprising: a cardiac pump housing; a cardiac pump rotor; a primary flow path and one, or more secondary flow paths wherein the secondary flow paths are at least partially configured to fluidically connect two or more regions of the primary flow path. The cardiac pump further comprises one or more plain bearing assemblies, the plain bearing assemblies comprising: a first bearing portion, the first bearing portion being configured to engage a second bearing portion. One of the first bearing portion and the second bearing portion are configured to rotate with the cardiac pump rotor. The first bearing portion comprises one or more first bearing surfaces and the second bearing portion comprising one or more second bearing surfaces. The one or more first bearing surfaces are configured so as to be in contact with the one or more second bearing surfaces so as to define a bearing interface between the one or more first bearing surfaces and the one or more second bearing surfaces during rotation of the cardiac pump rotor. The first bearing portion comprises one or more first flow channels configured to interrupt the bearing interface and permit blood to flow between an outside of the plain bearing assembly and a centre of the plain bearing assembly for the purpose of washing the bearing interface and preventing the deposition of proteins and/or the formation of thrombi. The one or more first flow channels at least partially form one or more of the secondary flow paths.

LIST OF FIGURES

For a better understanding of the present disclosure, and to show more clearly how it may be carried into effect, reference will now be made, by way of example, to the accompanying drawings, in which:

FIG. 3D shows a detailed view of a second bearing assembly according to the second embodiment of the plain bearing assembly an installed configuration in the second embodiment of a cardiac pump.

DETAILED DESCRIPTION

Figure 1:
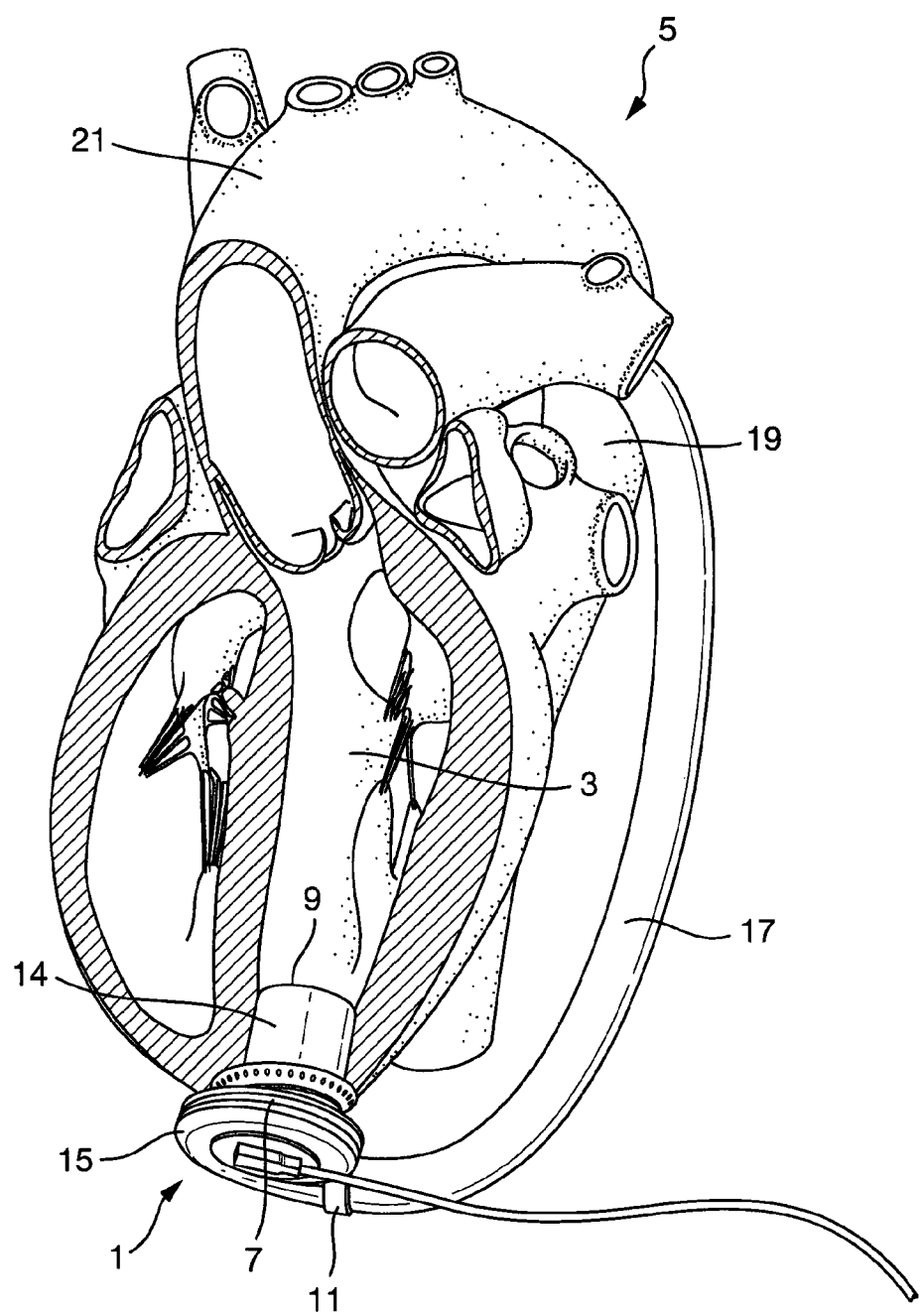
FIG. 1 shows a cut-away of a heart with a cardiac pump implanted into the left ventricle.

FIG. 1 depicts a cardiac pump 1 for the treatment of heat failure, e.g. a ventricular assist device, in an installed configuration in the left ventricle 3 of a heart 5. The cardiac pump 1 comprises a cardiac pump housing 7 comprising an inlet 9 for blood and an outlet 11 for blood. The cardiac pump 1 comprises a cardiac pump rotor disposed at least partially within the cardiac pump housing 7.

The cardiac pump 1 comprises an inflow cannula 14 situated at least partially inside the left ventricle 3 and a pumping chamber 15 situated outside of the heart 5. The inflow cannula 14 extends between the pumping chamber 15, through the wall of the left ventricle 3 into the chamber of the left ventricle 3, so that the inlet 9 is situated completely within the left ventricle 3. The pumping chamber 15 is situated on the apex of the left ventricle 3 with the outlet 11 connected to an outflow cannula 17. In the example shown in FIG. 1, the outflow cannula 17 is anastomosed to a descending aorta 19, although in an alternative example the outflow cannula 17 may be anastomosed to an ascending aorta 21.

The present invention relates to a plain bearing assembly for a cardiac pump that mitigates the risk of the deposition of proteins and/or the formation of thrombi in areas proximate to the plain bearing assembly. The plain bearing assembly is a type of hearing assembly in which the bearing surfaces are configured to be in contact during operation. For example, the plain bearing assembly may comprise no intermediate rolling elements, i.e. motion is transmitted directly between two or more contacted surfaces.

Figure 2A:
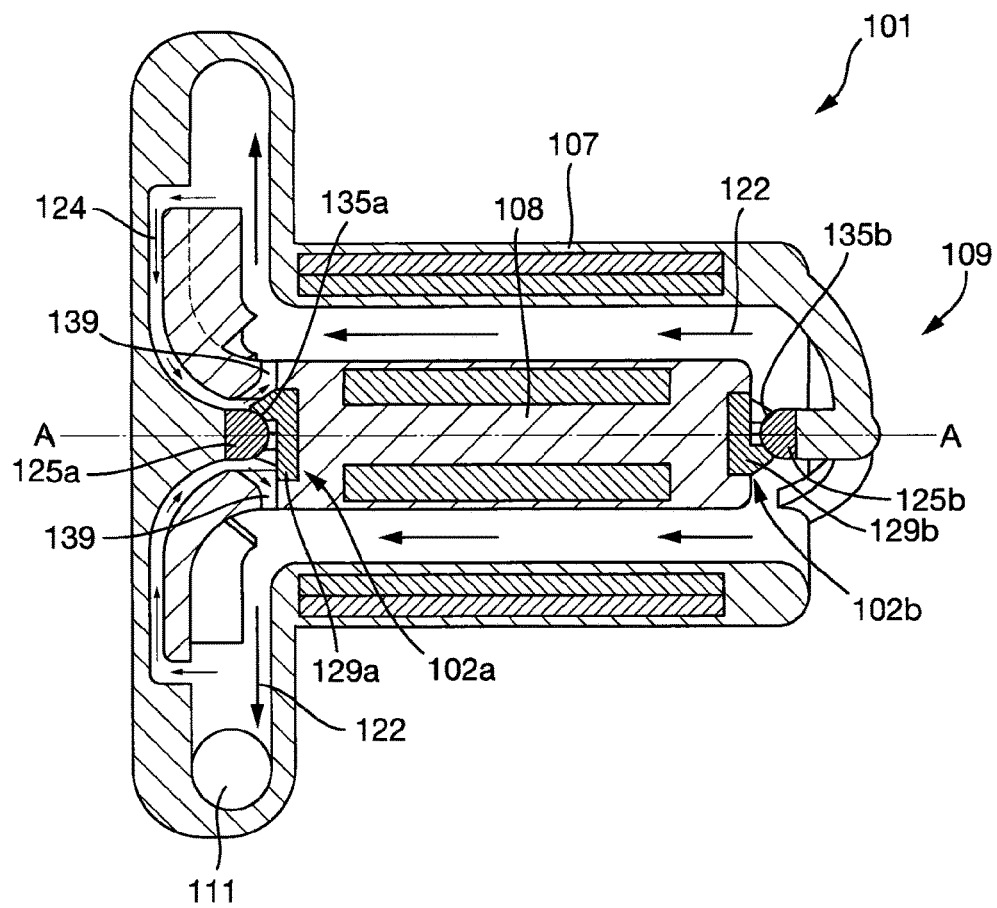
FIG. 2A shows a first embodiment of a plain bearing assembly according to the present invention in an installed configuration in a first embodiment of a cardiac pump.

First Embodiment of a Plain Bearing Assembly in a First Embodiment of a Cardiac Pump FIGS. 2A to 2D show a first embodiment of a plain bearing assembly 102 installed in a first embodiment of a cardiac pump 101. FIG. 2A shows a cross-section through the cardiac pump 101. The cardiac pump 101 comprises a cardiac pump housing 107 and a cardiac pump rotor 108. The cardiac pump rotor 108 is rotatably coupled to an impeller, which is configured to pump the blood. The cardiac pump rotor 108 is supported by one or more of the plain bearing assemblies 102. In the example shown in FIG. 2A, the cardiac pump rotor is substantially constrained, e.g. in five degrees-of-freedom by a first and a second plain bearing assembly 102a, 102b, such that the cardiac pump rotor 108 may rotate about a longitudinal axis A-A. The impeller may be provided at an end of the rotor with the first plain bearing assembly 102a.

A primary flow path 122 is defined as the flow of blood between the inlet 109 and the outlet 111 of the cardiac pump 101. A secondary flow path 124 is defined as any recirculating flow inside the cardiac pump 101 that does not form part of the primary flow path 122. The secondary flow path 124 may be configured to at least partially fluidically connect two or more regions of the primary flow path 122.

The plain bearing assembly 102 comprises one or more first bearing portions 129. The first bearing portion 129 comprises one or more first bearing surfaces 131. In the example shown in FIG. 2A, the plain bearing assemblies 102a, 102b comprise a first and a second first bearing portion 129a, 129b respectively. In use, the first bearing portions 129a, 129b rotate with the cardiac pump rotor 108. In the example shown in FIG. 2A, the first bearing portions 129a, 129b are fixed to the cardiac pump rotor 108, although in an alternative embodiment (not shown) the first bearing portions 129a, 129b may be integral to the cardiac pump rotor 108. The first bearing portions 129a, 129b may be constructed from a different material to the cardiac pump rotor 108, e.g. a ceramic material. The first bearing portions 129a, 129b may be constructed from a similar material to the cardiac pump housing, e.g. a titanium alloy. The first bearing portions 129a, 129b may comprise a surface coating and/or may have had a surface treatment to improve the wear characteristics of the plain bearing assemblies 102a, 102b.

The cardiac pump housing 107 comprises one or more second bearing portion 125. The second bearing portion 125 comprises one or more second bearing surfaces 127. In the example shown in FIG. 2A, the cardiac pump housing comprises a first and a second bearing portion 125a, 125b fixed to the cardiac pump housing 107, although in an alternative embodiment (not shown), the second bearing portions 125a, 125b may be integral to the cardiac pump housing 107. The second bearing portions 125a, 125b may be constructed from a different material to the cardiac pump housing 107, e.g. ceramic material. The second bearing portions 125a, 125b may be constructed from a similar material to the cardiac pump housing, e.g. a titanium alloy. The second bearing portions 125a, 125b may comprise a surface coating and/or may have had a surface treatment to improve the wear characteristics of the pain bearing assembly 102a, 102b.

The first bearing portions 129a, 129b are configured to engage the second bearing portions 125a, 125b respectively. The one or more first bearing surfaces 131a, 131b of the first bearing portions 129a, 129b are configured so as to be in contact with the one or more second bearing surfaces 127a, 127b of the second bearing portions 125a, 125b respectively during rotation of the cardiac pump rotor 108. A bearing interface 135a, 135b is defined between each of the one or more second bearing surfaces 127a, 127b and the one or more first bearing surfaces 131a, 131b during rotation of the cardiac pump rotor 108. Accordingly, in addition to the first bearing portions 129a, 129b, the plain bearing assemblies 102a, 102b may comprise the second bearing portions 125a, 125b respectively.

The first bearing portions 129a, 129b further comprise one or more first flow channels 133a, 133b. The first flow channels 133a, 133b are configured to interrupt, e.g. intersect, the bearing interface 135a, 135b and permit blood to flow between an outside 132a, 132b of the plain bearing assembly 102a, 102b and a centre 134a, 134b of the plain bearing assembly 102a, 102b. In other words, the first flow channels 133a, 133b may be open channels on the first bearing surfaces 131, e.g. the one or more first flow channels may be formed by one or more grooves through the one or more first bearing surfaces 131. The second bearing surfaces 127 may extend across the open side of the first flow channels 133a, 133b. The outside 132a, 132b of the plain bearing assembly 102a, 102b is the region radially outside the plain bearing assembly 102a, 102b and the centre 134a, 134b of the plain bearing assembly 102a, 102b is the region radially inside the plain bearing assembly 102a, 102b.

Figure 2B:
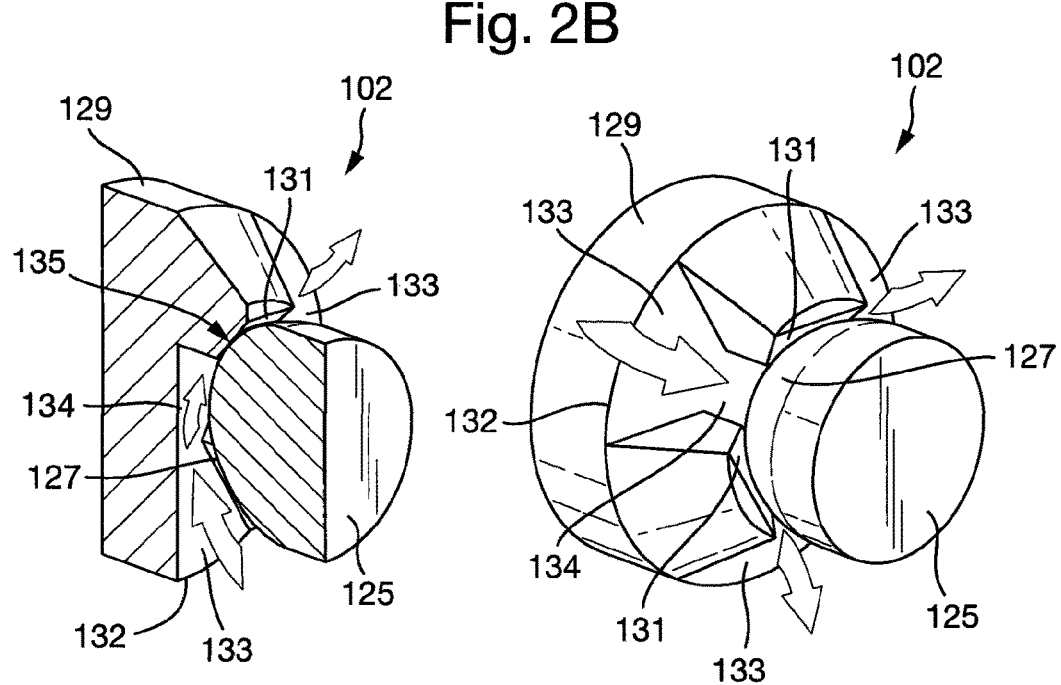
FIG. 2B shows the first embodiment of the plain bearing assembly according to the present invention in an uninstalled configuration.

FIG. 2B shows a detailed view of the first bearing portion 129 and the second bearing portion 125 of the plain bearing assembly 102 in an uninstalled configuration. The first bearing portion 129 comprises planar first bearing surfaces 131, which are provided on respective protrusions 137 of the first bearing portion 129. The second bearing portion 125 comprises a partially spherical second bearing surface 127. The first flow channels 133 are provided between the protrusions 137. The first and second bearing surfaces 131, 127 are configured such that upon engagement of the first and second bearing surfaces 131, 127, a bearing interface 135 is defined. In an installed configuration comprising the first and second bearing assemblies 102a, 102b, as in the embodiments described below for example, the first bearing portions 129 may thus be substantially constrained in five degrees-of-freedom about the second bearing portion 125.

In the first embodiment of the plain bearing assembly 102, the bearing interface 135 comprises three areas of point-contact between the partially spherical second bearing surface 127 and three planar first bearing surfaces 131. However, in an alternative embodiment (see FIGS. 3A to 4C described below), the plain bearing assembly 102 may comprises at least a partial ball and socket bearing, wherein the one or more second bearing surfaces 127 and the one or more first bearing surfaces 131 are substantially conformal. In general, the plain bearing assembly 102 may be configured such that the cardiac pump rotor 108 is substantially constrained in five degrees-of-freedom by any combination of point-, line- or surface-contact between the first and second bearing surfaces 131, 127 (see for example FIG. 5).

In the first embodiment of the plain bearing assembly 102 shown in FIGS. 2A to 2D, the first bearing portions 129a, 129b further comprise first flow channels 133a, 133b configured to interrupt the bearing interface 135a, 135b and permit blood to flow between the outside 132a, 132b of the plain bearing assembly 102a, 102b and the centre 134a, 134b of the plain bearing assembly 102a, 102b. It is anticipated that blood may flow in and/or out of each of the first bearing channels 133a, 133b for the purpose of providing a constant flow of blood that serves to wash the bearing interface 135a, 135b. Since the deposition of proteins and/or thrombus formation may be associated with areas of flow stasis, it may be seen as advantageous to provide a continuous flow of blood through the plain bearing assembly 102 and interrupt the circumferential contact between the first and second bearing surfaces 131, 127. The present invention serves to mitigate the predilection for areas of flow stasis that may be associated with deposition of proteins and/or thrombus formation, thus reducing the overall number of adverse events due to bearing malfunction and/or failure in implanted devices.

The cardiac pump rotor 108 may further comprise one or more second flow channels 139 that extend axially and/or radially through the cardiac pump rotor 108. The one or more second flow channels 139 may be fluidically connected to the one or more first flow channels 133 in the plain bearing assembly 102. The one or more first flow channels 133 in the plain bearing assembly 102 and/or the one or more second flow channels 139 in the cardiac pump rotor 108 may at least partially form the secondary flow path 124. The secondary flow path may be at least partially configured to connect two or more regions of the primary flow 122.

Figure 2C:
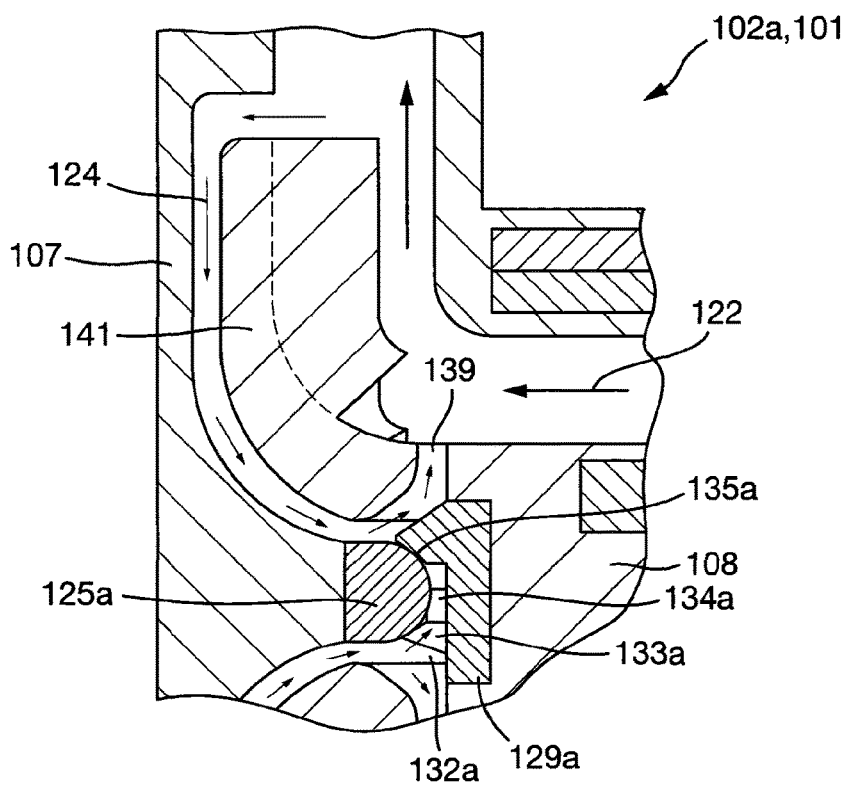
FIG. 2C shows a detailed view of a first bearing assembly according to the first embodiment of the plain bearing assembly in an installed configuration in the first embodiment of a cardiac pump.

In first embodiment of the cardiac pump 101 shown in FIGS. 2A and 2C, the cardiac pump rotor 108 comprises a plurality of second flow channels 139 that extend radially through the cardiac pump rotor 108, the second flow channels 139 being fluidically connected to the first flow channels 133a in the first plain bearing assembly 102a.

Figure 2D:
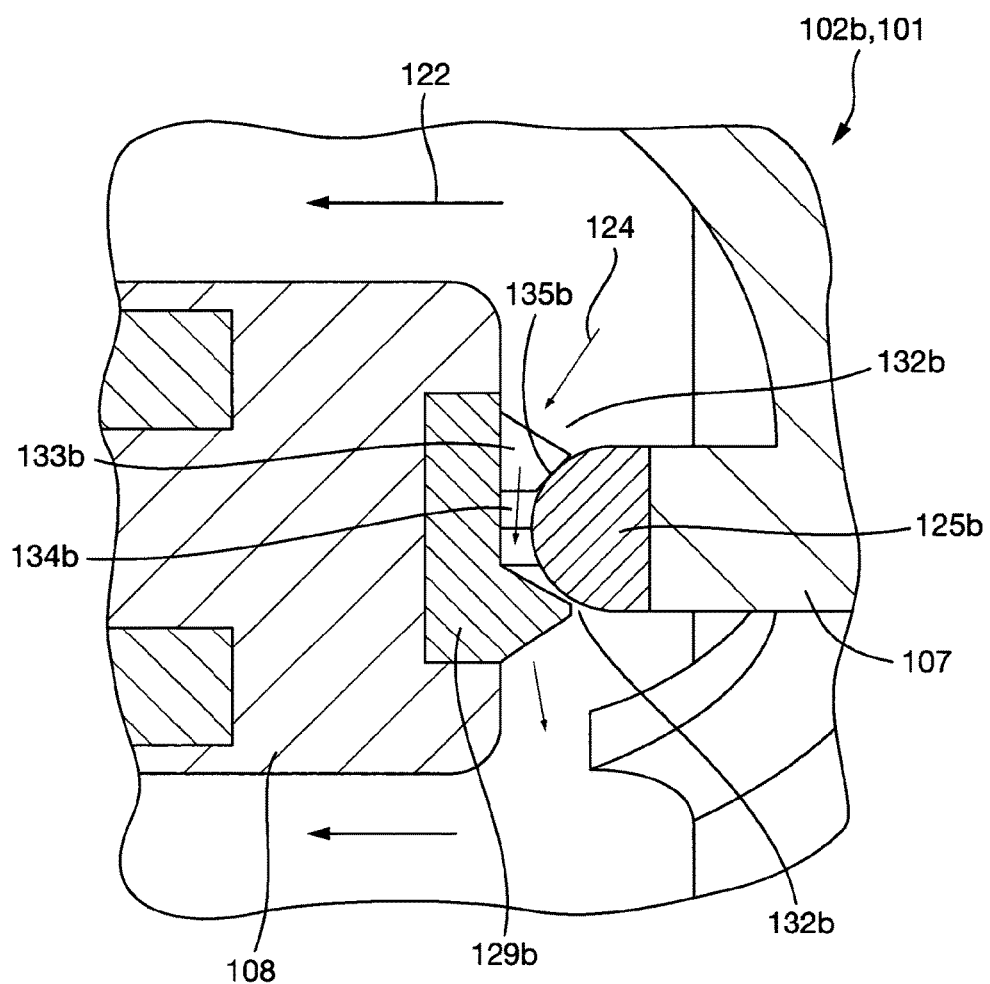
FIG. 2D shows a detailed view of a second bearing assembly according to the first embodiment of the plain bearing assembly in an installed configuration in the first embodiment of the cardiac pump.

FIGS. 2C and 2D show detailed views of the and second plain bearing assemblies 102a, 102b respectively in an installed configuration. FIG. 2C depicts how blood enters the secondary flow path 124 formed between an impeller shroud 141 of the cardiac pump rotor 108 and the cardiac pump housing 107. Blood flows from a high pressure region at an outer diameter of the impeller shroud 141 towards a lower pressure region at in inner diameter of the impeller shroud 141. The bearing interface 135a is situated in the secondary flow path 124. Consequently, the first flow channels 133a in the first bearing assembly 102a permit blood to flow between the outside 132a and the centre 134a of the first plain bearing assembly 102a. Since the second flow channels 139a the cardiac pump rotor 108 are fluidically connected to the first flow channels 133a, blood may flow between the centre 134a of the first plain bearing assembly 102a and the primary flow path 122. Consequently, the first flow channels 133a in the first bearing assembly 102a permit blood to flow between the outside 132a the centre 134a of the first plain bearing assembly 102a. In this way, the bearing interface 135a is supplied with a continuous flow of fresh blood for the purposes of washing the bearing interface 135a and disrupting any areas of flow stasis that may exist, therefore mitigating the risk of thrombus formation and/or the deposition of proteins in the region surrounding the plain bearing assembly 102a.

FIG. 2D depicts how blood enters the secondary flow path 124 formed by the first flow channels 133b in the second plain bearing assembly 102b. The first flow channels 133b fluidically connect the outside 132b and the centre 134b of the second plain bearing assembly 102b. Therefore, in a similar manner to the first bearing assembly 102a, the bearing interface 135b is supplied with a continuous flow of fresh blood for the purposes of washing the bearing interface 135b and disrupting any areas of flow stasis that may exist, therefore mitigating the risk of thrombus formation end/or the deposition of proteins in the region surrounding the plain bearing assembly 102a.

Second Embodiment of a Plain Bearing Assembly in a Second Embodiment of a Cardiac Pump FIGS. 3A to 3D show a second embodiment of plain bearing assembly 202 installed in a second embodiment of a cardiac pump 201. The plain bearing assembly 202 for the cardiac pump 201 comprises similar features to those described above, the benefits of which apply equally to the embodiments described below. Features of the first embodiments apply equally to the second embodiment and any additional and/or alternative features are described below. For the sake of brevity, those similar features share similar reference numerals, e.g. the first embodiment of the plain bearing assembly 102 and the second embodiment of the plain bearing assembly 202.

Figure 3A:
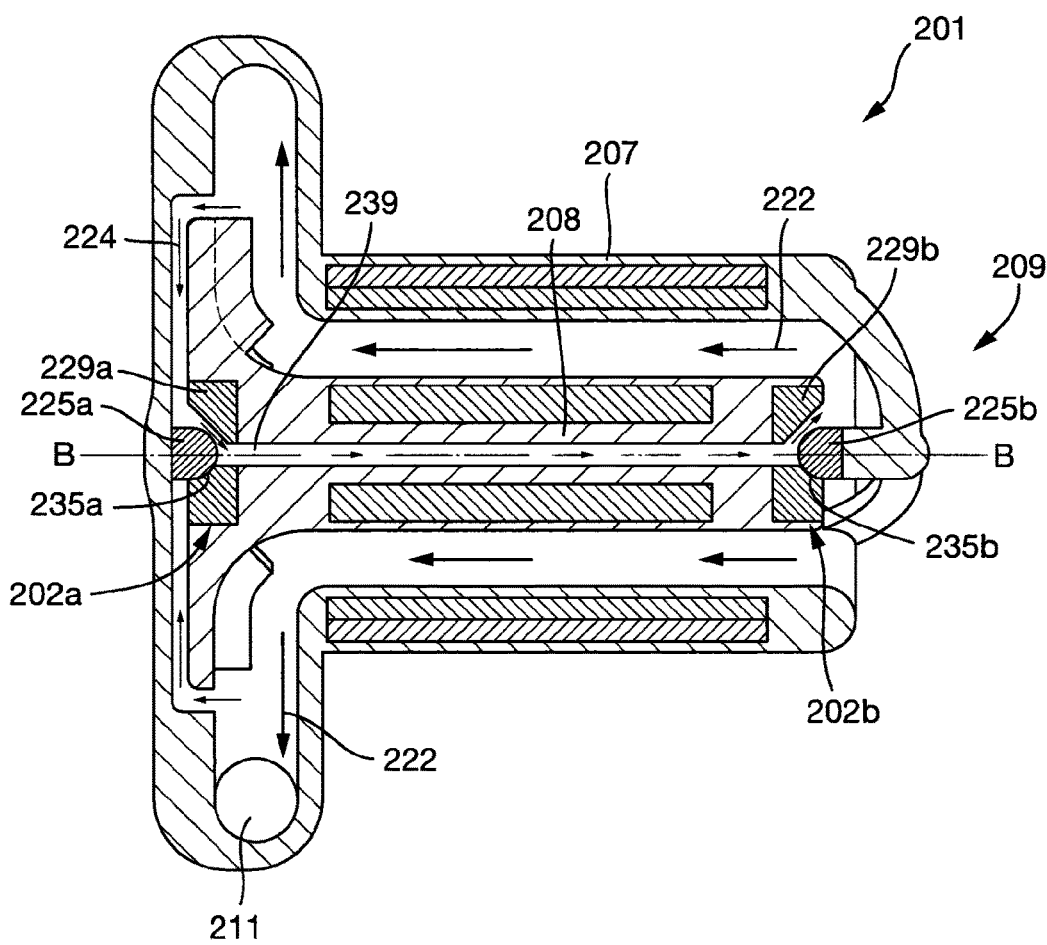
FIG. 3A shows a second embodiment of a plain bearing assembly according to the present invention in an installed configuration in a second embodiment of a cardiac pump.

FIG. 3A shows cross-section of the cardiac pump 201. The cardiac pump 201 comprises a cardiac pump housing 207 and a cardiac pump rotor 208. The cardiac pump rotor 208 is supported by one or more plain bearing assemblies 202. In the example shown in FIG. 3A, the cardiac pump rotor 208 is substantially constrained, e.g. in five degrees-of-freedom, by a first and a second plain bearing assembly 202a, 202b, such that the cardiac pump rotor 208 may rotate about a longitudinal axis B-B.

Figure 3B:
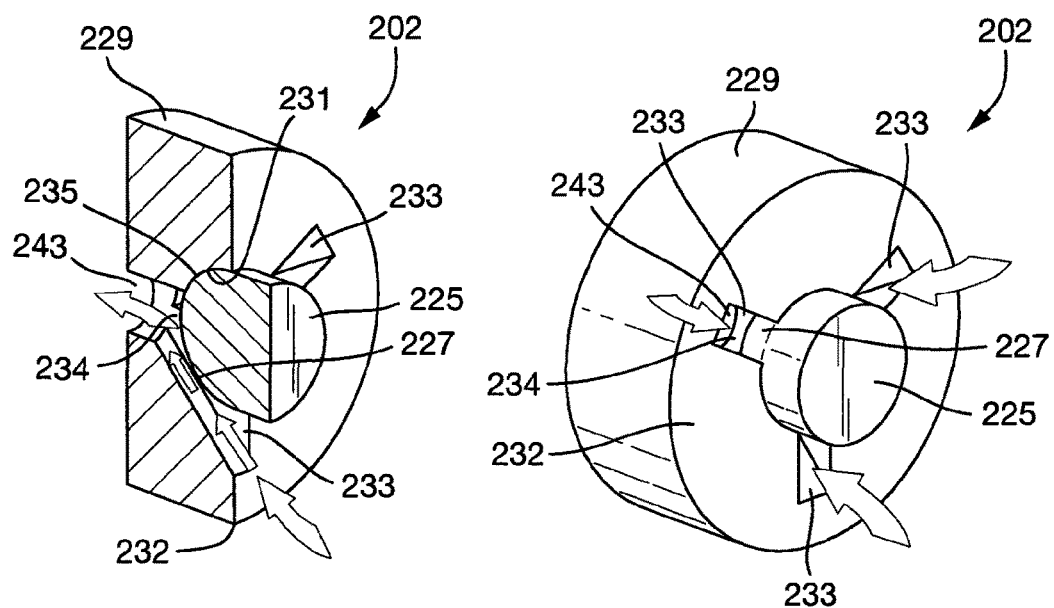
FIG. 3B shows the second embodiment of the plain bearing assembly according the present invention in an uninstalled configuration.

FIG. 3B shows a detailed view of the first bearing portion 229 and the second bearing portion 225 of the plain bearing assembly 202 in an uninstalled configuration. The plain bearing assembly 202 comprises a ball and socket type bearing assembly, wherein the second bearing portion 225 comprises a partially spherical second bearing surface 227. The first bearing portion 229 comprises a correspondingly-shaped first bearing surface 231. The first bearing surface 231 is interrupted by first flow channels 233, thereby forming discrete first bearing surfaces 231 that share a common partially spherical boundary. The first bearing surfaces 231 and the second bearing surface 227 and are substantially conformal. The first and second bearing surfaces 231, 227 are configured such that upon engagement of the first and second bearing surfaces 231, 227, a bearing interface 235 is defined.

The first bearing portion 229 father comprises an opening 243 that extends axially through the first bearing portion 229. The opening 243 is configured to intersect the first flow channels 233 and permit blood to flow through the first bearing portion 229. In an alternative embodiment (not shown), the first bearing portion 229 may not comprise the opening 243. It may be appreciated, therefore, that in such an alternative embodiment, blood may flow in and/or out of the first flow channels 233 in a similar manner and with those similar benefits as described for the first embodiment of the plain bearing assembly.

It is also appreciated that the first bearing surfaces 231 may be planar, or indeed of any form, e.g. frusto-conical.

The cardiac pump rotor 208 may further comprise one or more second flow channels 239 that extend axially and/or radially through the cardiac pump rotor 208. The one or more second flow channels 239 may be fluidically connected to the one or more first flow channels 233 in the pain bearing assembly 202. The one or more first flow channels 233 in the plain bearing assembly 202 and the one or more second flow channels 239 in the cardiac pump rotor 208 may at least partially the secondary flow path 224. The secondary flow path may be at least partially configured to cot two or more regions of the primary flow 222.

The one or more second flow chancels 239 of the cardiac pump rotor 208 may be configured to fluidically connect the one or more first flow channels 233a of the first plain bearing assembly 202a to the one or more first flow channels 233b of the second plain bearing assembly 202b, such that blood may flow between the outside 232a of the first plain bearing assembly 202a and the outside 232b of the second plain bearing assembly 202b.

Figure 3C:
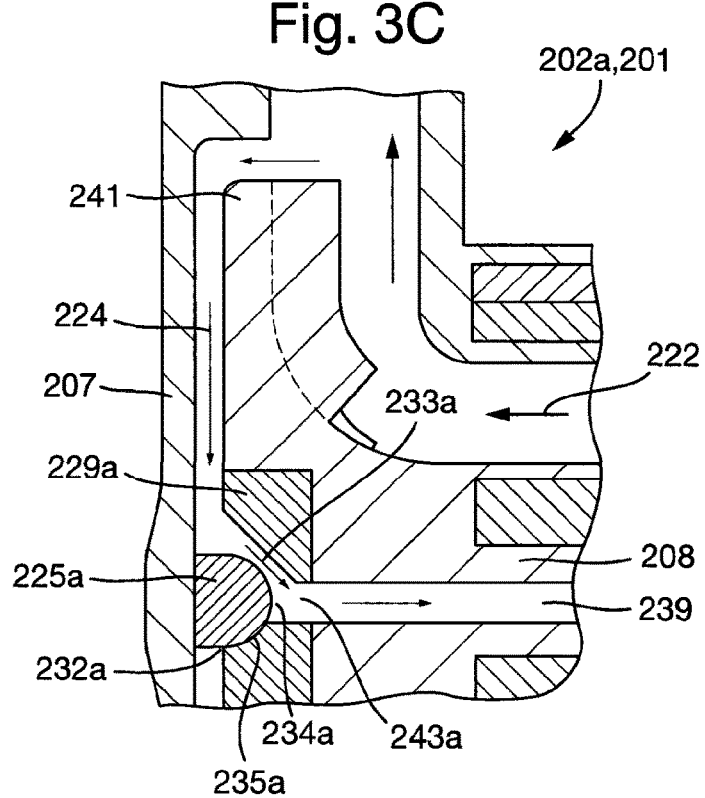
FIG. 3C shows a detailed view of a first bearing assembly according to the second embodiment of the plain bearing assembly in an installed configuration in the second embodiment of the cardiac pump.

In the second embodiment of the cardiac pump 201 shown in FIGS. 3A, 3C and 3D, the cardiac pump rotor 208 comprises the second flow channel 239 that extends axially through the length of the cardiac pump rotor 208. The second flow channel 239 is configured to fluidic ally connect the first flow channels 233a in the first plain bearing assembly 202a to the first flow channels 233b in the first plain bearing assembly 202b.

FIGS. 3C and 3D show detailed views of the first and second plain bearing assemblies 202a, 202b respectively in an installed configuration. FIG. 3C depicts how blood eaters the secondary flow path 224 formed between an impeller shroud 241 of the cardiac pump rotor 208 and the cardiac pump housing 207. Blood flows from a high pressure region at an outer diameter of the impeller shroud 241 towards a lower pressure region at in inner diameter of the impeller shroud 241. The bearing interface 235a is situated in the secondary flow path 224. Consequently, the first flow channels 233a in the first plain bearing assembly 202a permit blood to flow between the outside 232a and the centre 234a of the first plain bearing assembly 202a. Since the opening 243a extends axially through the first bearing portion 229a, intersecting the first flow channels 233a, blood is further permitted to flow through the first bearing portion 229 and into the second flow channel 239 in the cardiac pump rotor 208.

FIG. 3D depicts ho blood flows through the second flow channel 239 in the cardiac pump rotor 208 and through the second plain bearing assembly 102b. The second flow channel 239 is configured to connect the opening 243b in the first bearing portion 229b of the second plain bearing assembly 202b to the opening 243a in the first bearing portion 229a of the first plain bearing assembly 202a. Consequently, blood is further permitted to flow between the second flow channel 239 in the cardiac pump rotor 208 and the first flow channels 233b in the first bearing portion 229b.

Hence, the outside 232a of the first plain bearing assembly 202a is fluidically connected to the outside 232b of the second plain bearing assembly 202b by virtue of the first flow channels 233a, 233b, the openings 243a, 243b and the second flow channel 239. A secondary flow path is defined therefore between the outer diameter of the impeller shroud 241 and the outside 234b of the second plain bearing assembly 202b. In this manner, the bearing interfaces 235a, 235b are supplied with a continuous flow of fresh blood for the purposes of washing the bearing interfaces 235a, 235b and disrupting any areas of flow stasis that may exist, therefore mitigating the risk of thrombus formation and/or the deposition of proteins in the region surrounding the first and second plain bearing assemblies 202a, 202b.

Second Embodiment of a Plain Bearing Assembly in a Third Embodiment of a Cardiac Pump FIGS. 4A to 4D describe the second embodiment of the plain bearing assembly 202 installed in a third embodiment of a cardiac pump 301. The plain bearing assembly 202 for the cardiac pump 301 comprises similar features to those described above, the benefits of which apply equally to the embodiments described below. Features of the first and second embodiments apply equally to the third embodiment and any additional and/or alternative features are described below. For the sake of brevity, it is assumed those similar features share similar reference numerals, e.g. the second embodiment of the cardiac pump 201 and the third embodiment of the cardiac pump 301. Any additional and/or alternative features are described below.

Figure 4A:
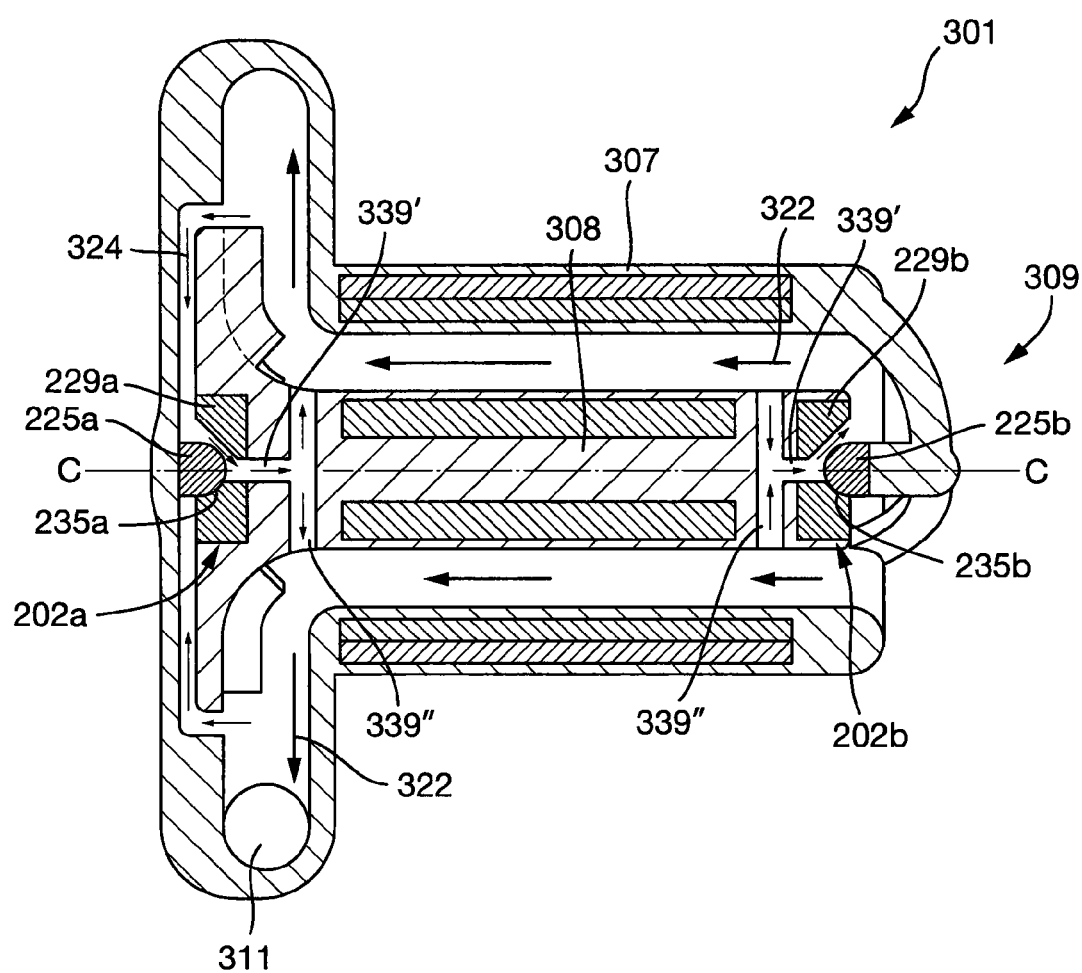
FIG. 4A shows the second embodiment of the plain bearing assembly according to the present invention in an installed configuration in a third embodiment of a cardiac pump.

FIG. 4A shows a cross-section of the cardiac pump 301. The cardiac pump 301 comprises a cardiac pump housing 307 and a cardiac pump rotor 308. The cardiac pump rotor 308 is supported by one or more plain bearing assemblies 202 as described above. In the example shown in FIG. 4A, the cardiac pump rotor 308 is substantially constrained, e.g. in five degrees-of-freedom, by the first and a second plain bearing assembly 202a, 202b, such that the cardiac pump rotor 308 may rotate about a longitudinal axis C-C.

The cardiac pump rotor 305 may further comprise one or more second flow channels 339 that extend axially and/or radially through the cardiac pump rotor 308. The one or more second flow channels 339 in the cardiac pump may be fluidically connected to the one or more first flow channels 233 in the plain bearing assembly 202. The one or more first flow channels 233 in the plain bearing assembly 202 and the one or more second flow channels 339 in the cardiac pump rotor 308 may at least partially form the secondary flow path 324. The secondary flow path may be at least partially configured to connect two or more regions of the primary flow 322.

Figure 4B:
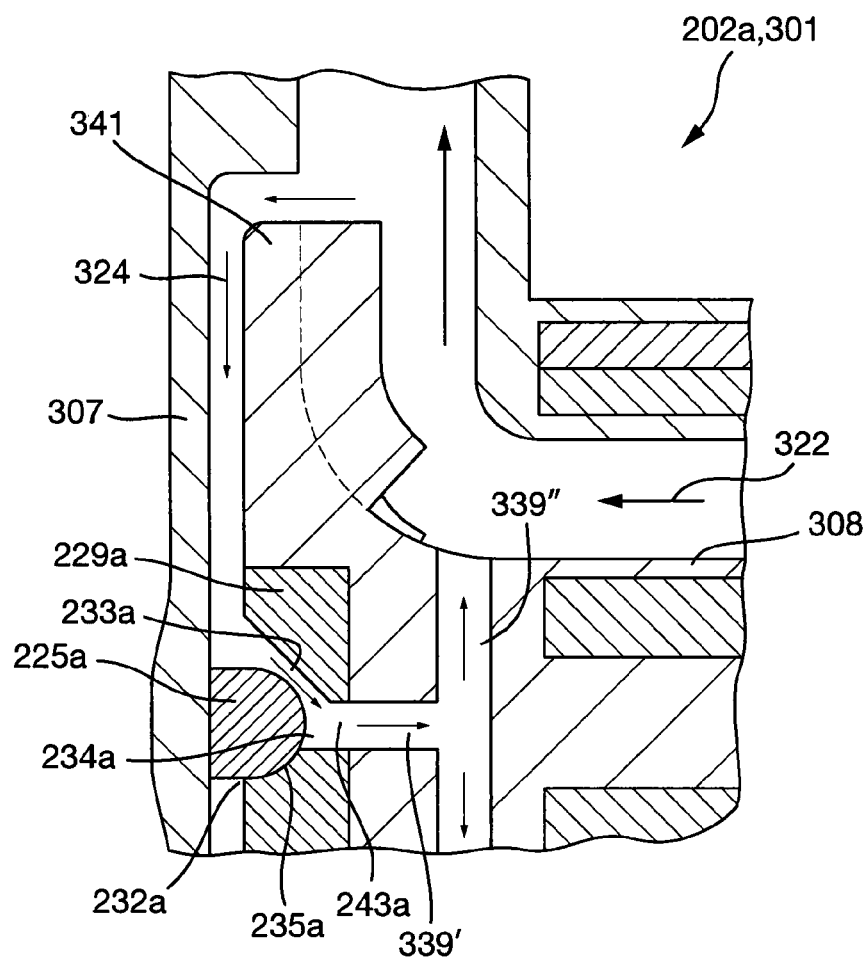
FIG. 4B shows a detailed view of the first bearing assembly according to the second embodiment of the plain bearing assembly in at it/staged configuration in the third embodiment of the cardiac pump.
Figure 4C:
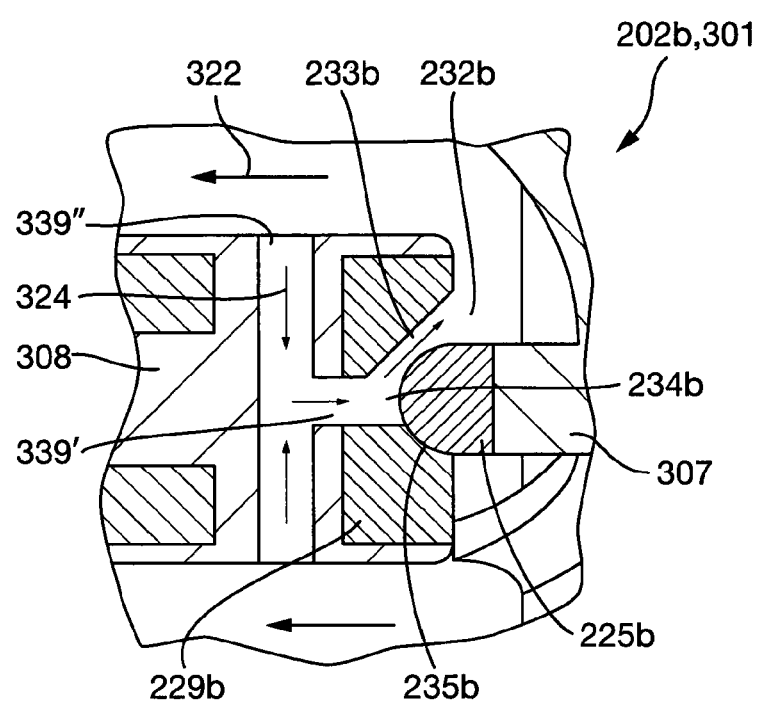
FIG. 4C shows a detailed view of a second bearing assembly according to the second embodiment of the plain bearing assembly in an in tailed configuration in the third embodiment of the cardiac pump.

In the third embodiment of the cardiac pump 301 shown in FIGS. 4A to 4C, the cardiac pump rotor 308 comprises one or more axial second flow channels 339' that at least partially extend axially through the length of the cardiac pump rotor 308. The cardiac pump rotor 308 further comprises one or more radial second flow channels 339" that at least partially extend radially through the cardiac pump rotor 308. The one or more axial second flow channels 339' are configured to fluidically connect the one or more radial second flow channels 339" to the first flow channels 233 in the first plain bearing assembly 202.

FIGS. 4B and 4C show detailed views of the first and second plain bearing assemblies 202a, 202b respectively in an installed configuration. FIG. 4C depicts how blood flows through the first plain bearing assembly 202a. Blood enters the secondary flow path 324 formed between an impeller shroud 341 of the cardiac pump rotor 308 and the cardiac pump housing 307. Blood flows from a high pressure region at an outer diameter of the impeller shroud 341 towards a tower pressure region at in inner diameter of the impeller shroud 341. The bearing interface 235a is situated in the secondary flow path 224. Consequently, the first flow channels 233a in the second bearing assembly 202a permit blood to flow between the outside and the centre 234a of the first plain bearing assembly 202a. Since the opening 243a extends axially through the first bearing portion 229a, intersecting the first flow channels 233a, blood is further permitted to flow from the through the first bearing portion 229 into the axial second flow channel 339' and the radial second flow channels 339" in the cardiac pump rotor 308.

Hence, the outside 232a of the first plait bearing assembly 202a is fluidically connected to the primary flow path 322 by virtue of the first flow channels 233a the opening 243a and the axial and radial second flow channels 339', 339". A secondary flow path 324 is defined therefore between the outer diameter of the impeller shroud 241 and the primary flow path 322. In this manner, the bearing interfaces 235a is supplied with a continuous flow of fresh blood for the purposes of washing the bearing interfaces 135a and disrupting any areas of flow stasis that may exist, therefore mitigating the risk of thrombus formation and/or the deposition of proteins in the region surrounding the first plain bearing assembly 202a.

FIG. 4C depicts how blood flows through the second plain bearing assembly 202b. Blood enters the secondary flow path 324 formed between the outer diameter of the cardiac pump rotor 308 and the outside of the second plain bearing assembly 202b. The bearing interface 235b is situated in the secondary flow path 324. Consequently, the first flow channels 333b in the second bearing assembly 202b permit blood to flow between the outside 232b and the centre 234b of the first plain bearing assembly 202b. Since the opening 243b extends axially through the first bearing portion 229b intersecting the first flow channels 233b, blood is further permitted to flow between the first bearing portion 229, the axial second flow channel 339' and the radial second flow channels 339" in the cardiac pump rotor 308.

Hence, the outside 232b of the second plain bearing assembly 202b is fluidically connected to the primary flow path 322 by virtue of the first flow channels 233b the opening 243b and the axial and radial second flow channels 339', 339". A further secondary flow path 324 is defined therefore between the outer diameter of the cardiac pump rotor 308 and the primary flow path 322. In this manner, the bearing interfaces 235b is supplied with a continuous flow of fresh blood for the purposes of washing the bearing interfaces 235b and disrupting any areas of flow stasis that may exist, therefore mitigating the risk of thrombus formation and/or the deposition of proteins in the region surrounding the second plain bearing assembly 202b.

Third Embodiment of a Plain Bearing Assembly for a Cardiac Blood Pump

Figure 5:
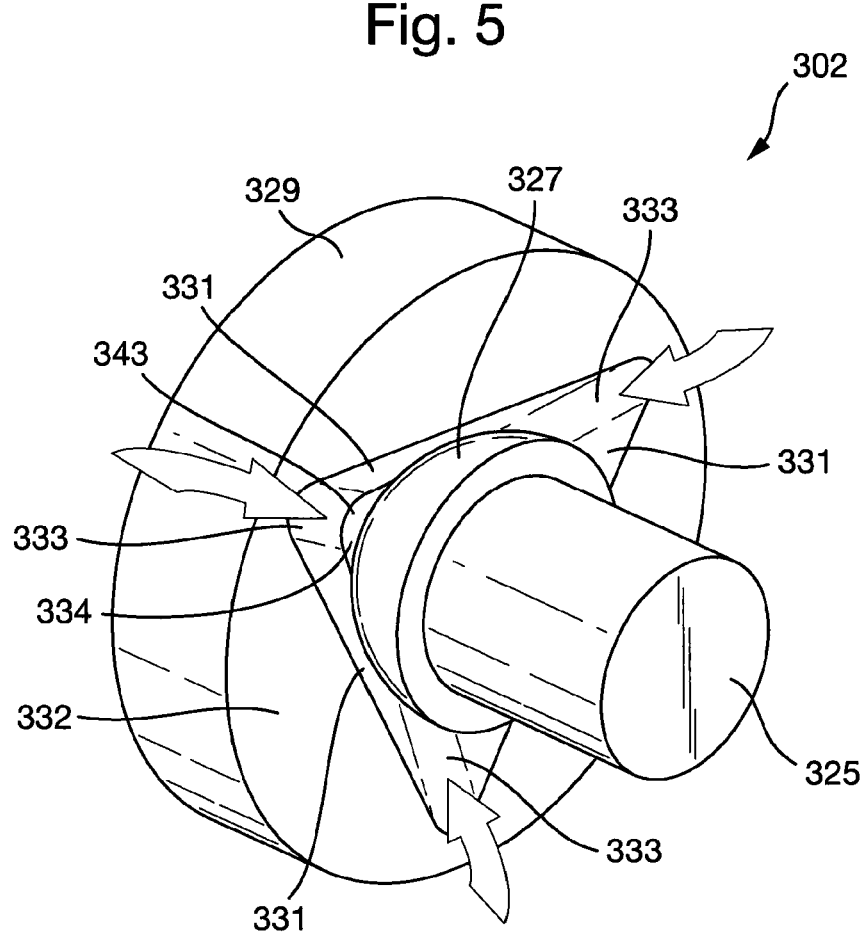
FIG. 5 shows a third embodiment a plain bearing assembly according to the present invention in an uninstalled configuration.

FIG. 5 depicts a third embodiment of the plain bearing assembly 302 for the cardiac pump 1. The plain bearing assembly 302 for the cardiac pump 1 comprises similar features to those described above, the benefits of which apply equally to the embodiments described below. Features of the previously described embodiments apply equally to the third embodiment and any additional and/or alternative features are described below. For the sake of brevity, it is assumed those similar features share similar reference numerals, e.g. the third embodiment of the plain bearing assembly 302 and second embodiment of the plain bearing assembly 202. Any additional and/or alternative features are described below.

FIG. 5 shows a detailed view of the first bearing portion 329 and the second bearing portion 325 of the plain bearing assembly 302 in an uninstalled configuration. The first bearing portion 329 comprises three or more planar second bearing surfaces 331, which are provided in a recess 337 of the first bearing portion 329. The second bearing portion 325 comprises a partially spherical first bearing surface 327. The first and second bearing surfaces 331, 327 are configured such that upon engagement of the first and second bearing surfaces 331, 327, a bearing interface 335 is defined.

In the third embodiment of plain bearing assembly 302 shown in FIG. 5, the recess 337 is provided by a tetrahedron-shaped out-out in the first bearing portion 329. However, in an alternative embodiment (not shown), the recess 337 may be provided by any shaped cut-out that may rotatably receive the first bearing portion 329, e.g. by virtue of any combination of point-, line- or surface-contacts.

The first bearing portion 329 may further comprise one or more first flow channels 333 configured to interrupt the bearing interface 335 and permit blood to flow between the outside 332 of the plain bearing assembly 302 and the centre 334 of the plain bearing assembly 302. The plain bearing assembly 302 may be further configured such that one or more of the second bearing surfaces 331 forms a continuous surface with one or more walls of the adjacent one or more first flow channels 333. In the third embodiment of the plain bearing assembly 302 shown in FIG. 5, the three planar bearing surfaces 331 each form a continuous surface with the walls of the adjacent first flow channels 333.

Hence, in an installed configuration (not shown), blood is permitted to flow between the outside 332 and the centre 334 of the plain bearing assembly 302. In this manner, the bearing interface 335 are supplied with a continuous flow of fresh blood for the purposes of washing the bearing interfaces 335 and disrupting any areas of flow stasis that may exist, therefore mitigating the risk of thrombus formation and/or the deposition of proteins in the region surrounding the plain bearing assembly 302.

The first bearing portion 329 further comprises an opening 343 that extends axially through the first bearing portion 329. The opening 343 is configured to intersect the first flow channels 333 and permit blood to flow through the first bearing portion 329. In an alternative embodiment (not shown), the first bearing portion 329 may not comprise the opening 343. It may be appreciated, therefore, that in such an alternative embodiment, blood may flow in and/or out of the first flow channels 333 in a similar manner and with those similar benefits as described for the first embodiment of the plain bearing assembly 102.

It may be generally appreciated that the described embodiments of the plain bearing assemblies 102, 202, 302 may not be confined to use with their associated embodiments of the cardiac pump 101, 201, 301. Indeed, each of the described plain bearing assemblies 102, 202, 302 in accordance with the present invention may be installed in any of the described embodiments or any other appropriate cardiac pump.

REFERENCE NUMERALS 1, 101, 201, 301 cardiac pump
3 left ventricle
5 heart
7, 107, 207, 307 cardiac pump housing
8, 108, 208, 308 cardiac pump rotor
9, 109 net
11, 111 outlet
14 inflow cannula
15 pumping chamber
16 left ventricular wall
17 outflow cannula
19 descending aorta
21 ascending aorta
102, 202, 302 plain bearing assembly
102a, 202a first plain bearing assembly
102b, 202b second plain bearing assembly
122, 222, 322 primary flow path
124, 224, 324 secondary flow path
125, 225, 325 stationary portion
127, 227, 327 first bearing surface
129, 229, 329 rotational portion
131, 231, 331 second bearing surface
132, 132a, 132b, 232, 232a, 232b, 332 outside of the plain bearing assembly
133, 133a, 133b, 233, 233a, 233b, 333 first flow channels
134, 134a, 134b, 234, 234a, 234b, 334 centre of the plain bearing assembly
135, 135a, 135b, 235, 235a, 235b, 335 bearing interface
137 protrusion
139, 139a, 139b, 239a, 239b, 339, 339', 339" second low channels
141, 241 impeller shroud

The invention claimed is:

1. A plain bearing assembly for a cardiac pump, the plain bearing assembly comprising:
a first bearing portion;
a second bearing portion;
one of the first bearing portion or the second bearing portion configured to rotate about a longitudinal axis relative to the other of the first bearing portion or the second bearing portion;
the first bearing portion having a first end surface on the longitudinal axis and at least one first bearing surface on a bearing axis, the bearing axis spaced away from the longitudinal axis;
the second bearing portion having a second end surface on the longitudinal axis and at least a second bearing surface on the bearing axis, the bearing axis spaced away from the longitudinal axis;
the at least one first bearing surface and the at least one second bearing surface define a bearing interface on the bearing axis and spaced away from the longitudinal axis to define a space at a radial centre of the plain bearing assembly on the longitudinal axis and between the first end surface and second end surface; and
at least one first flow channel formed into the first bearing portion to interrupt the bearing interface to permit blood to flow from radially outside the bearing interface to the space at the radial centre of the plain bearing assembly on the longitudinal axis and between the first end surface of the first bearing portion on the longitudinal axis and spaced apart from the second end surface of the second bearing portion on the longitudinal axis.

2. A plain bearing assembly for a cardiac pump, the plain bearing assembly comprising:
a first bearing portion;
a second bearing portion;
one of the first bearing portion or the second bearing portion being configured to rotate with a cardiac pump rotor about a longitudinal axis;
the first bearing portion comprising one or more first bearing surfaces on one or more bearing axes and the second bearing portion comprising one or more second bearing surfaces on the one or more bearing axes;
the one or more first bearing surfaces and the one or more second bearing surfaces define a bearing interface between the one or more first bearing surfaces and the one or more second bearing surfaces on the one or more bearing axes during rotation of the cardiac pump rotor about the longitudinal axis, the one or more bearing axes spaced away from the longitudinal axis;

the first bearing portion comprising a first end surface on the longitudinal axis;
the second bearing portion comprising a second end surface on the longitudinal axis; and
the first bearing portion comprising one or more first flow channels configured to interrupt the bearing interface and direct blood flow from radially outside of the bearing interface to a space at the radial centre of the plain bearing assembly on the longitudinal axis and between the first end surface of the first bearing portion and the second end surface of the second bearing portion, the space at the radial centre of the plain bearing assembly is defined as the space between the first end surface of the first bearing portion on the longitudinal axis and spaced apart from the second end surface of the second bearing portion on the longitudinal axis.

3. The plain bearing assembly according to claim 2, wherein the first bearing portion further comprises an opening extending axially through the first bearing portion, the opening being configured to intersect the one or more first flow channels and permit blood to flow through the first bearing portion.

4. The plain bearing assembly according to claim 2, wherein the one or more first bearing surfaces and the one or more second bearing surfaces are substantially conformal and radially spaced away from the longitudinal axis and the centre is positioned on the longitudinal axis and defines the space between the first bearing portion and the second bearing portion.

5. The plain bearing assembly according to claim 2, wherein the one or more first flow channels are formed by one or more grooves through the one or more first bearing surfaces to the centre of the plain bearing assembly on the longitudinal axis.

6. The plain bearing assembly according to claim 2, wherein the plain bearing assembly comprises at least a partial ball and socket bearing, the socket bearing being the first bearing portion and the partial ball being the second bearing portion, the centre of the plain bearing assembly being further defined as the space between a distal end of the partial ball on the longitudinal axis and a spaced apart socket bearing portion on the longitudinal axis.

7. The plain bearing assembly according to claim 2, wherein the plain bearing assembly comprises at least a partial ring and cone bearing.

8. The plain bearing assembly according to claim 2, wherein one or more of the second bearing surfaces forms a continuous surface with one or more walls of the adjacent one or more first flow channels.

9. The plain bearing assembly according to claim 2, wherein the one or more first flow channels are created by one or more gaps between a non-axisymmetric first bearing surface and an axisymmetric second bearing surface.

10. The plain bearing assembly according to claim 2, wherein the one or more first bearing surfaces are configured to at least partially form the shape of a pyramid.

11. A cardiac pump comprising one or more plain bearing assemblies of claim 2.

12. The cardiac pump according to claim 11, the cardiac pump further comprising a primary flow path and one or more secondary flow paths, the secondary flow paths being at least partially configured to fluidically connect two or more regions of the primary flow path.

13. The cardiac pump according to claim 12, wherein the one or more first flow channels in the plain bearing assembly at least partially form the secondary flow path.

14. The cardiac pump according to claim 11, wherein the cardiac pump rotor comprises one or more second flow channels that extend through the cardiac pump rotor.

15. The cardiac pump according to claim 14, wherein the one or more second flow channels in the cardiac pump rotor at least partially form the secondary flow path.

16. The cardiac pump according to claim 14, wherein the one or more first flow channels in the plain bearing assembly are fluidically connected to the one or more second flow channels in the cardiac pump rotor.

17. The cardiac pump according to claim 14, wherein the one or more second flow channels are configured to extend through the cardiac pump rotor and be fluidically connected with the one or more first flow channels, such that blood may flow between the outside of the plain bearing assembly and the one or more second flow channels through the cardiac pump rotor.

18. The cardiac pump according to claim 14, the cardiac pump further comprising a first plain bearing assembly and a second plain bearing assembly, wherein the one or more second flow channels of the cardiac pump rotor fluidically connect the one or more first flow channels of the first plain bearing assembly to the one or more first flow channels of the second plain bearing assembly, such that blood may flow between the outside of the first plain bearing assembly and the outside of the second plain bearing assembly.

19. The plain bearing assembly according to claim 2, wherein one or more first flow channels extend to the centre on the longitudinal axis to define the space between the first and second bearing portions.

20. A cardiac pump comprising:
a cardiac pump housing;
a cardiac pump rotor extending along a longitudinal axis;
a primary flow path and one or more secondary flow paths, wherein the secondary flow paths are at least partially configured to fluidically connect two or more regions of the primary flow path;
one or more plain bearing assemblies, the plain bearing assemblies comprising:
a first bearing portion;
a second bearing portion;
one of the first bearing portion or the second bearing portion being configured to rotate with the cardiac pump rotor about the longitudinal axis, the first bearing portion comprising one or more first bearing surfaces on one or more bearing axes and the second bearing portion comprising one or more second bearing surfaces on the one or more bearing axes;
the one or more first bearing surfaces and the one or more second bearing surfaces define a bearing interface on the one or more bearing axes, the one or more bearing axes spaced away from the longitudinal axis;
the first bearing portion comprising a first end surface on the longitudinal axis;
the second bearing portion comprising a second end surface on the longitudinal axis;
the first bearing portion comprising one or more first flow channels configured to interrupt the bearing interface and direct blood flow from radially outside of the bearing interface to a centre void of the plain bearing assembly, the centre void of the plain bearing assembly is on the longitudinal axis;
wherein the centre void of the plain bearing assembly is defined as a space on the longitudinal axis between the first end surface of the first bearing portion on the longitudinal axis and spaced apart from the second end surface of the second bearing portion on the longitudinal axis; and wherein the one or more first flow channels at least partially form one or more of the secondary flow paths.

21. The cardiac pump according to claim 20, wherein the interface between the one or more first bearing surfaces and the one or more second bearing surfaces is spaced away from the longitudinal axis and the centre defined by the space between the first bearing portion and the second bearing portion is further defined by the space between a first wall of the first bearing portion spaced apart from a second wall of the second bearing portion on the longitudinal axis.

* * * * *

UNITED STATES PATENT AND TRADEMARK OFFICE
CERTIFICATE OF CORRECTION

PATENT NO. : 10,195,324 B2
APPLICATION NO. : 14/895822
DATED : February 5, 2019
INVENTOR(S) : Graham Foster Page 1 of 4

It is certified that error appears in the above-identified patent and that said Letters Patent is hereby corrected as shown below:

On the Title Page

Item (72):
Before "West", insert --Swansea,-- therefore;

Column 2, Line 1, Other Publications:
Delete "Internationational" and insert --International-- therefore;

Column 2, Line 3, Page 2, Other Publications:
Delete "Internationational" and insert --International-- therefore;

In the Specification

Column 1, Line 44, Background:
After "a", insert --more-- therefore;

Column 1, Line 54, Background:
Delete "lit" and insert --fit-- therefore;

Column 2, Line 5, Background:
Delete "to" and insert --techniques,-- therefore;

Column 2, Line 44, Background:
After "axial", insert --flow-- therefore;

Column 2, Line 54, Background:
After "discloses", insert --a-- therefore;

Column 3, Line 10, Statements of Invention:
After "pump,", insert --the-- therefore;

Signed and Sealed this
Seventh Day of May, 2019

Andrei Iancu
*Director of the United States Patent and Trademark Office*

CERTIFICATE OF CORRECTION (continued)
U.S. Pat. No. 10,195,324 B2

Column 3, Line 24, Statements of Invention:
Delete "en" and insert --an-- therefore;

Column 3, Line 45, Statements of Invention:
After "bearing", insert --portion-- therefore;

Column 3, Line 49, Statements of Invention:
After "comprise", insert --a-- therefore;

Column 4, Line 22, Statements of Invention:
After "purpose", insert --of-- therefore;

Column 4, Line 39, Statements of Invention:
Delete "one," and insert --one-- therefore;

Column 5, Line 23, List of Figures:
After "according", insert --to-- therefore;

Column 5, Line 31, List of Figures:
After "assembly", insert --in-- therefore;

Column 5, Line 39, List of Figures:
Delete "at it/staged" and insert --and installed-- therefore;

Column 5, Line 43, List of Figures:
Delete "in tailed" and insert --installed-- therefore;

Column 5, Line 45, List of Figures:
After "embodiment", insert --of-- therefore;

Column 5, Line 51, Detailed Description:
Delete "heat" and insert --heart-- therefore;

Column 6, Line 8, Detailed Description:
Delete "hearing" and insert --bearing-- therefore;

Column 7, Line 1, Detailed Description:
Before "ceramic", insert --a-- therefore;

Column 7, Line 6, Detailed Description:
Delete "pain" and insert --plain-- therefore;

Column 8, Line 42, Detailed Description:
After "the", insert --first-- therefore;

CERTIFICATE OF CORRECTION (continued)
U.S. Pat. No. 10,195,324 B2

Column 8, Line 55, Detailed Description:
After "139a", insert --in-- therefore;

Column 9, Line 10, Detailed Description:
Delete "end/or" and insert --and/or-- therefore;

Column 9, Line 18, Detailed Description:
After "of", insert --a-- therefore;

Column 9, Line 30, Detailed Description:
After "shows", insert --a-- therefore;

Column 9, Line 55, Detailed Description:
Delete "father" and insert --further-- therefore;

Column 10, Line 5, Detailed Description:
Delete "pain" and insert --plain-- therefore;

Column 10, Line 9, Detailed Description:
After "partially", insert --form-- therefore;

Column 10, Line 10, Detailed Description:
Delete "cot" and insert --connect-- therefore;

Column 10, Line 12, Detailed Description:
Delete "chancels" and insert --channels-- therefore;

Column 10, Line 24, Detailed Description:
Delete "fluidic ally" and insert --fluidically-- therefore;

Column 10, Line 27, Detailed Description:
Delete "202b." and insert --202a.-- therefore;

Column 10, Line 30, Detailed Description:
Delete "eaters" and insert --enters-- therefore;

Column 10, Line 46, Detailed Description:
Delete "ho" and insert --how-- therefore;

Column 10, Line 62, Detailed Description:
Delete "234b" and insert --232b-- therefore;

Column 11, Line 29, Detailed Description:
Delete "305" and insert --308-- therefore;

CERTIFICATE OF CORRECTION (continued)
U.S. Pat. No. 10,195,324 B2

Column 11, Line 60, Detailed Description:
Delete "tower" and insert --lower-- therefore;

Column 11, Line 63, Detailed Description:
Delete "202a" and insert --202b-- therefore;

Column 11, Line 64, Detailed Description:
After "outside", insert --232a-- therefore;

Column 12, Line 25, Detailed Description:
Delete "202b." and insert --202a.-- therefore;

Column 12, Line 26, Detailed Description:
Delete "229b" and insert --229b,-- therefore;

Column 13, Line 1, Detailed Description:
Delete "331, 327" and insert --237, 331-- therefore;

Column 13, Line 3, Detailed Description:
Delete "331, 327," and insert --327, 331,-- therefore;

Column 13, Line 4, Detailed Description:
After "of", insert --the-- therefore;

Column 13, Line 6, Detailed Description:
Delete "out-out" and insert --cut-out-- therefore;

Column 13, Line 59, Reference Numerals:
Delete "net" and insert --inlet-- therefore;

Column 14, Line 16, Reference Numerals:
After "139b," insert --239-- therefore;

Column 14, Line 16, Reference Numerals:
Delete "low" and insert --flow-- therefore.